US012797206B2

(12) United States Patent
Stein et al.

(10) Patent No.: US 12,797,206 B2
(45) Date of Patent: Nov. 17, 2026

(54) LORDOTIC EXPANDABLE INTERBODY IMPLANT AND METHOD OF USING SAME

(71) Applicant: NuVasive, INC., San Diego, CA (US)

(72) Inventors: Christopher Stein, Fallbrook, CA (US); Seth Gustine, Encinitas, CA (US)

(73) Assignee: Globus Medical Inc., Audubon, PA (US)

(*) Notice: Subject to any disclaimer, the term of this patent is extended or adjusted under 35 U.S.C. 154(b) by 0 days.

(21) Appl. No.: 19/014,831

(22) Filed: Jan. 9, 2025

(65) Prior Publication Data

US 2025/0143891 A1 May 8, 2025

Related U.S. Application Data

(63) Continuation of application No. 18/321,043, filed on May 22, 2023, now Pat. No. 12,213,893, which is a continuation of application No. 16/667,766, filed on Oct. 29, 2019, now Pat. No. 11,696,836, which is a continuation of application No. 15/799,554, filed on Oct. 31, 2017, now Pat. No. 10,492,924, which is a continuation of application No. 14/456,640, filed on Aug. 11, 2014, now Pat. No. 9,801,734.

(60) Provisional application No. 61/864,132, filed on Aug. 9, 2013.

(51) Int. Cl.
*A61F 2/44* (2006.01)
*A61F 2/30* (2006.01)

(52) U.S. Cl.
CPC .... *A61F 2/447* (2013.01); *A61F 2002/30158* (2013.01); *A61F 2002/30387* (2013.01); *A61F 2002/30471* (2013.01); *A61F 2002/30507* (2013.01); *A61F 2002/30538* (2013.01); *A61F 2002/30904* (2013.01)

(58) Field of Classification Search
CPC ..................................................... A61F 2/4455
See application file for complete search history.

(56) References Cited

U.S. PATENT DOCUMENTS

| | | | | |
|---|---|---|---|---|
| 6,176,882 B1 * | 1/2001 | Biedermann | A61F 2/447 | 623/17.11 |
| 6,454,807 B1 * | 9/2002 | Jackson | A61F 2/447 | 623/17.15 |
| 6,641,614 B1 * | 11/2003 | Wagner | A61F 2/4455 | 623/17.15 |
| 8,366,777 B2 * | 2/2013 | Matthis | A61F 2/4465 | 623/17.11 |
| 8,382,842 B2 * | 2/2013 | Greenhalgh | A61F 2/447 | 623/17.11 |
| 8,597,360 B2 * | 12/2013 | McLuen | A61F 2/447 | 623/17.16 |
| 8,709,086 B2 * | 4/2014 | Glerum | A61F 2/4611 | 606/279 |
| 9,198,772 B2 * | 12/2015 | Weiman | A61F 2/4425 | |
| 9,216,095 B2 * | 12/2015 | Glerum | A61F 2/4611 | |
| 9,492,288 B2 * | 11/2016 | Wagner | A61F 2/4611 | |

(Continued)

*Primary Examiner* — David W Bates

(57) ABSTRACT

An expandable spinal fusion implant including a housing, upper and lower endplates, a wedge positioned within the housing and between the upper and lower endplates and a drive mechanism to urge the wedge distally between the upper and lower endplates to increase the separation between the endplates and expand the overall height of the distal end of the implant.

10 Claims, 18 Drawing Sheets

(56) References Cited

U.S. PATENT DOCUMENTS

| | | | | |
|---|---|---|---|---|
| 9,788,971 | B1 * | 10/2017 | Stein | A61F 2/447 |
| 10,159,583 | B2 * | 12/2018 | Dietzel | A61F 2/4657 |

* cited by examiner

LORDOTIC EXPANDABLE INTERBODY IMPLANT AND METHOD OF USING SAME

CROSS REFERENCE TO RELATED APPLICATIONS

This application is a continuation application of U.S. patent application Ser. No. 18/321,043, filed on May 22, 2023 and published as U.S. 2023-0285164, which is a continuation application of U.S. patent application Ser. No. 16/667,766, filed on Oct. 29, 2019 and now U.S. Pat. No. 11,696,836, which is a continuation application of U.S. patent application Ser. No. 15/799,554 filed on Oct. 31, 2017 and now U.S. Pat. No. 10,492,924, which is a continuation application of U.S. patent application Ser. No. 14/456,640, filed on Aug. 11, 2014 and now U.S. Pat. No. 9,801,734, which claims priority to U.S. Provisional Application No. 61/864,132 filed on Aug. 9, 2013, each of which is incorporated by reference in its entirety herein.

BACKGROUND

This application relates to expandable interbody spinal fusion implants and methods of using the same.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure. The expandable spinal fusion implant and related methods disclosed herein boasts a variety of inventive features and components that warrant patent protection, both individually and in combination.

In general, the expandable spinal fusion implants described in this document include a housing, upper and lower endplates, a translating wedge positioned between the upper and lower endplates and within the housing, and a drive mechanism to drive translation of the wedge. The expandable spinal fusion implant is designed to be inserted into the disc space between adjacent vertebral bodies from a posterior approach. The implant may be made of any suitable, biocompatible material or combination of materials. For example, the implant components may be metal, polyether ether ketone (PEEK), or a combination of the metal and PEEK. The implant is configured to be inserted into the disc space in a collapsed state and upon being seated in a desired location within the disc space the distal end of the implant is expanded in height to create an implant with a lordotic angle (i.e. the anterior height of the implant is greater than the posterior height of the implant, thereby restoring a more natural lordotic curvature of the particular segment of the lumbar spine). The expansion is accomplished by engaging the drive mechanism with a tool to activate the drive mechanism and cause the translating wedge to move between the implants in a distal direction.

Figure 1:
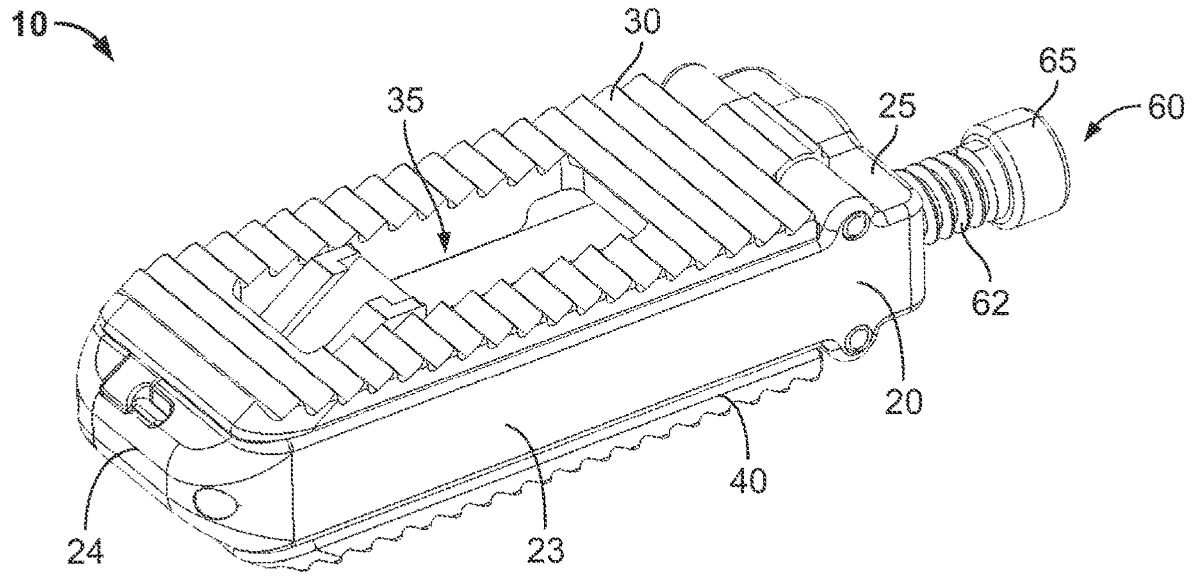
FIG. 1 is a perspective view of an expandable spinal fusion implant in a collapsed position, according to an exemplary embodiment.
Figure 2:
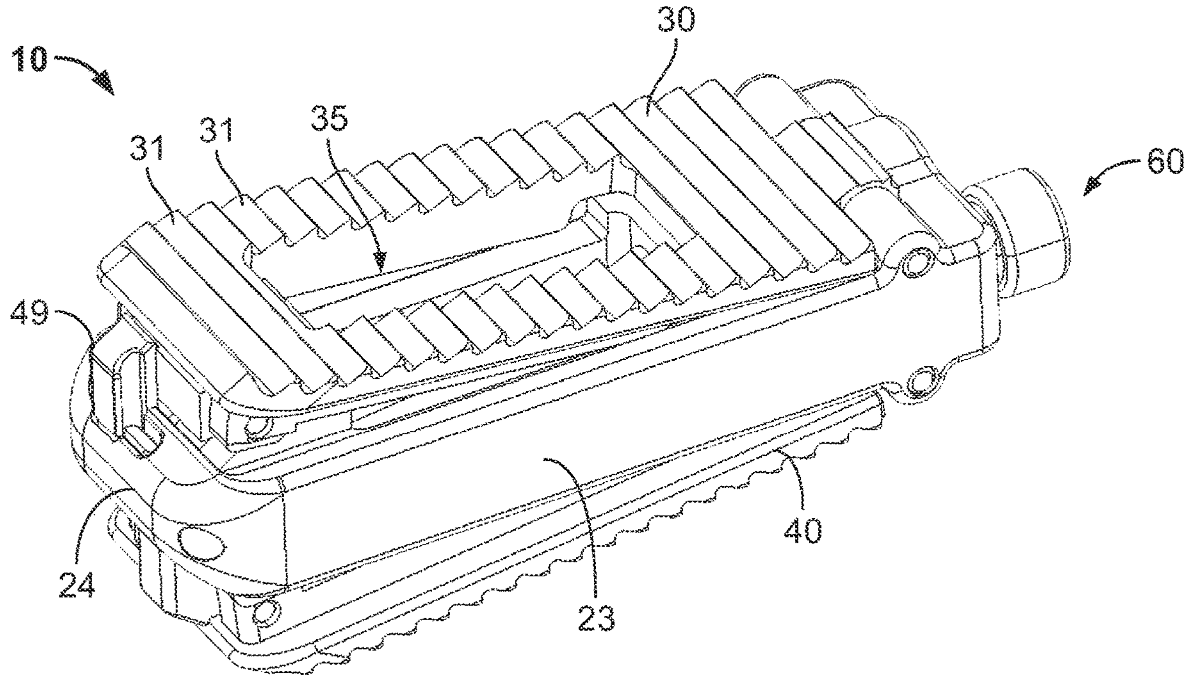
FIG. 2 is a perspective view of the expandable spinal fusion implant of FIG. 1 in an expanded position.
Figure 3:
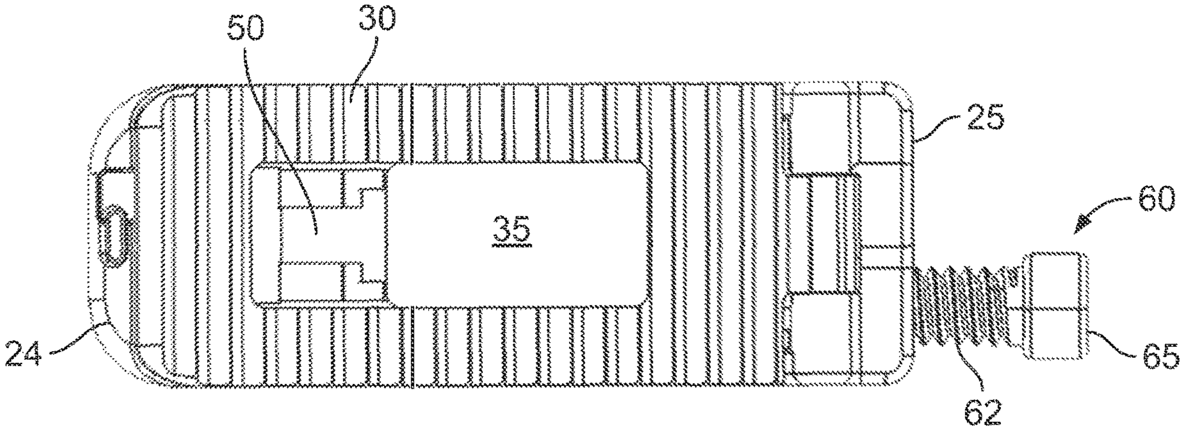
FIG. 3 is a top view of the expandable spinal fusion implant of FIG. 1.
Figure 4:
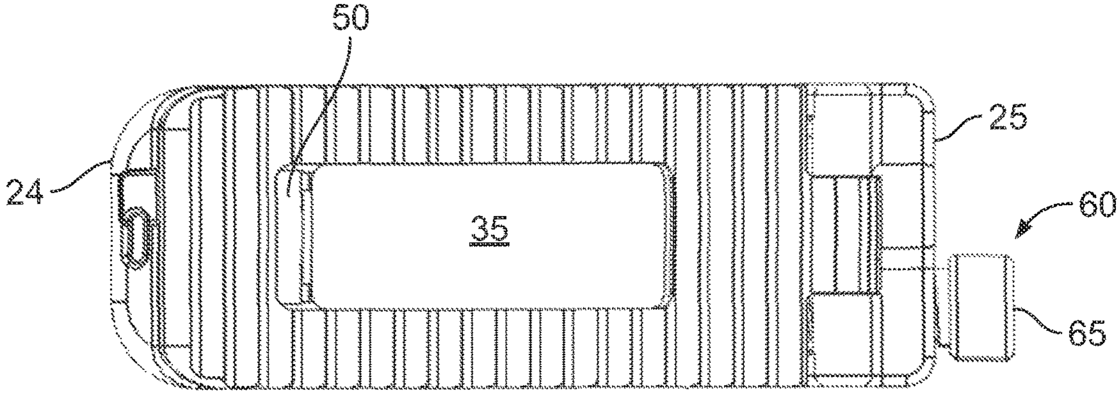
FIG. 4 is a top view of the expandable spinal fusion implant of FIG. 2.
Figure 5:
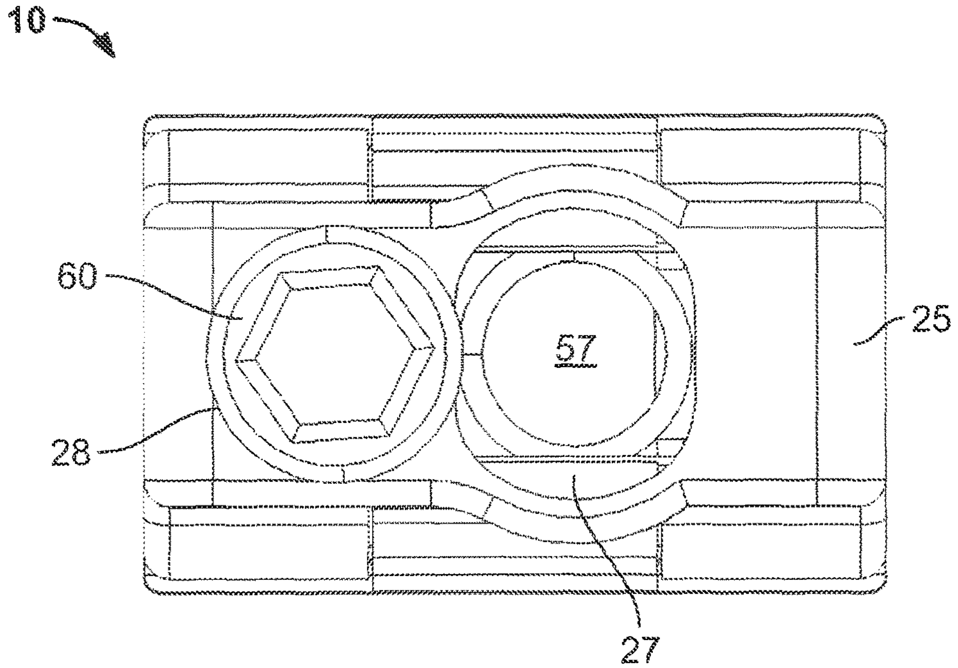
FIG. 5 is a back view of the expandable spinal fusion implant of FIG. 1.
Figure 6:
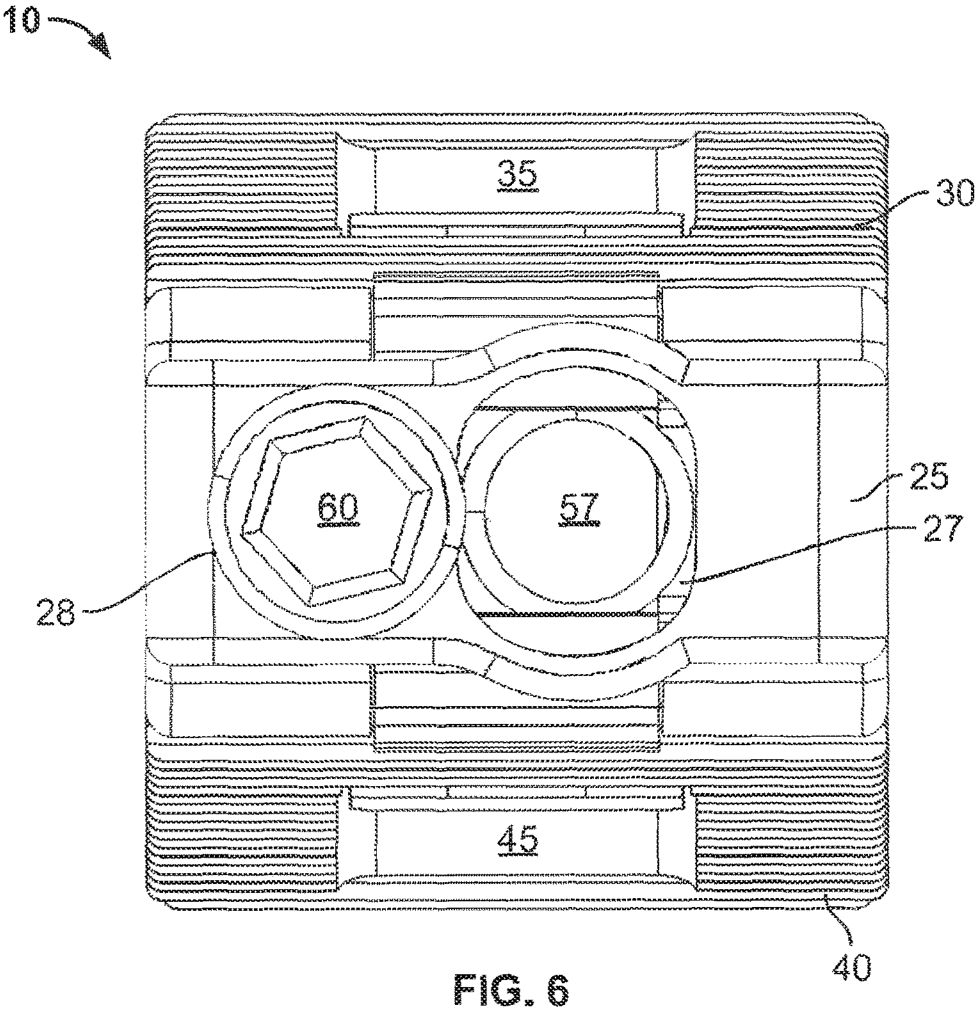
FIG. 6 is a back view of the expandable spinal fusion implant of FIG. 2.
Figure 7:
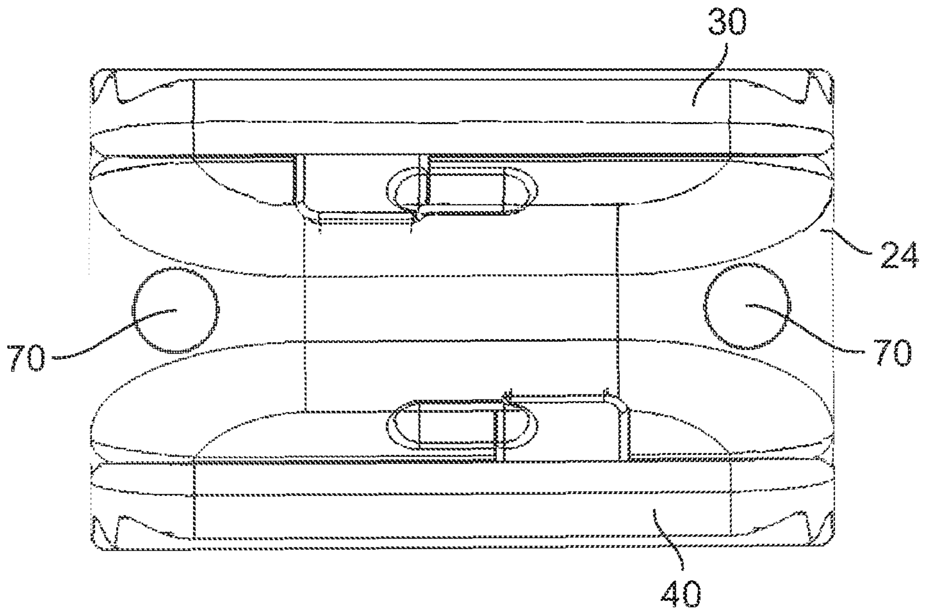
FIG. 7 is a front view of the expandable spinal fusion implant of FIG. 1.
Figure 8:
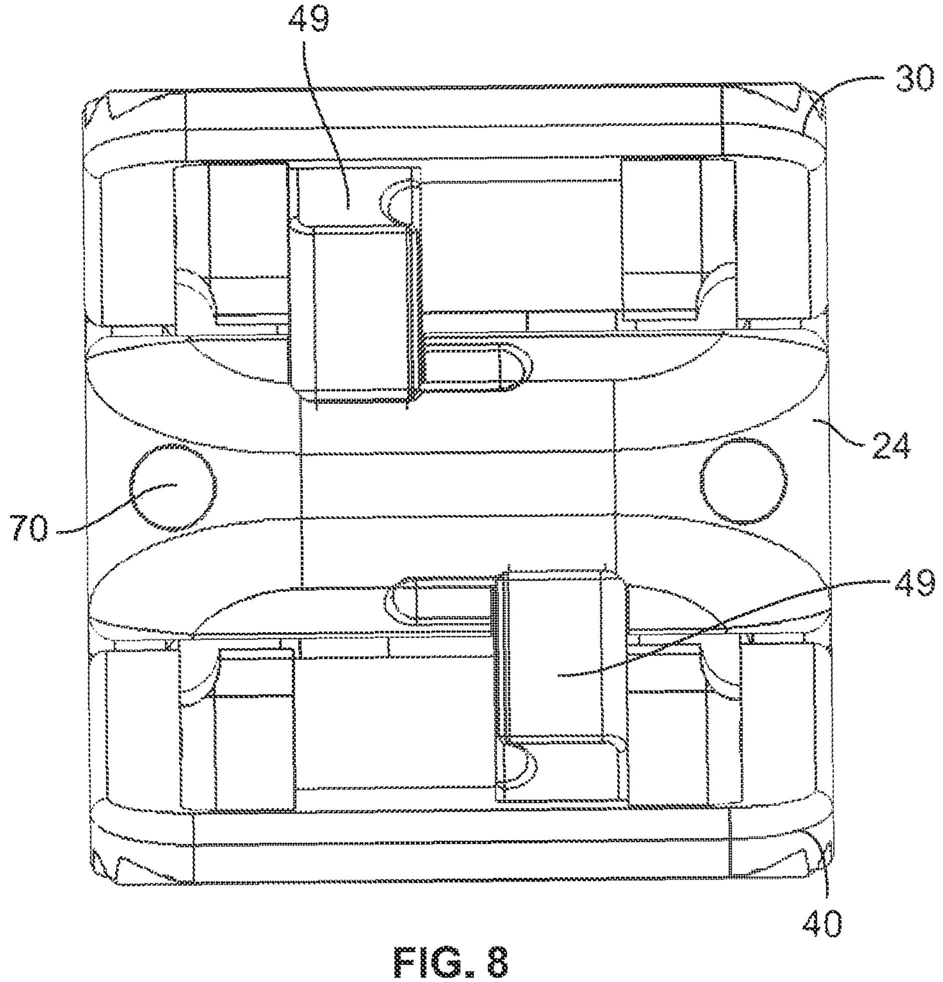
FIG. 8 is a front view of the expandable spinal fusion implant of FIG. 2.
Figure 9:
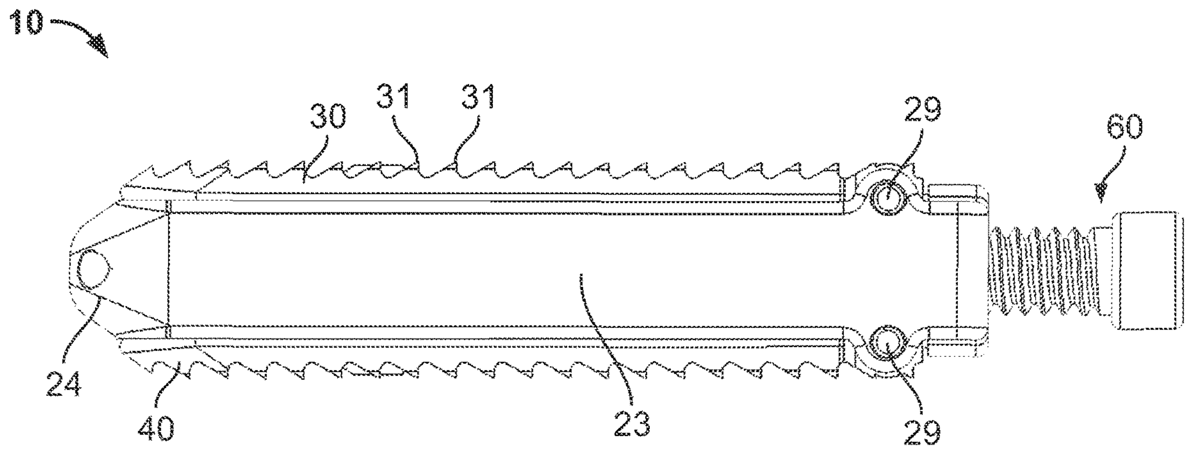
FIG. 9 is a side view of the expandable spinal fusion implant of FIG. 1.
Figure 10:
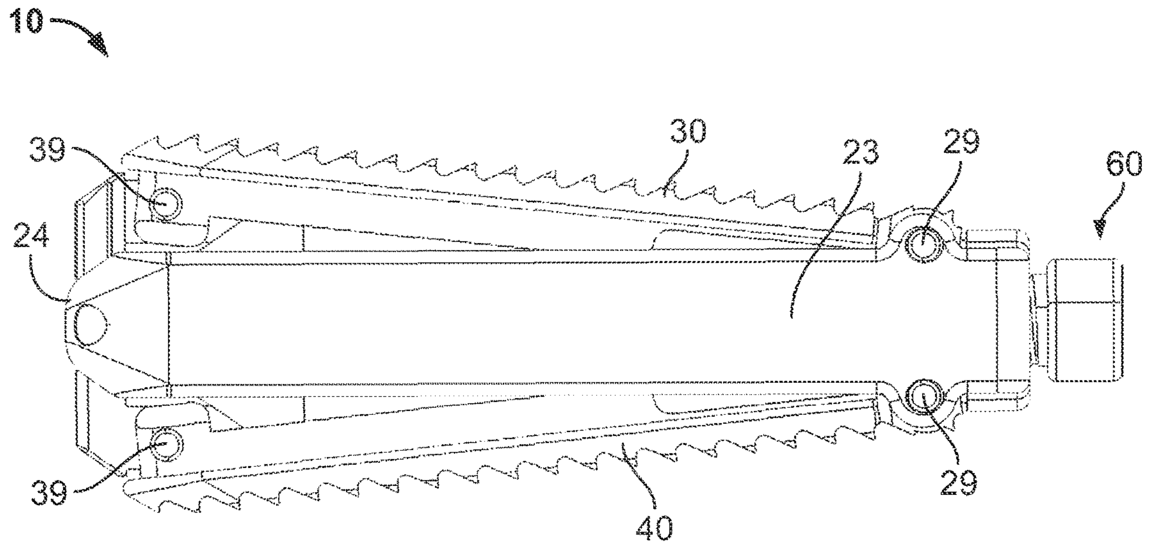
FIG. 10 is a side view of the expandable spinal fusion implant of FIG. 2.
Figure 11:
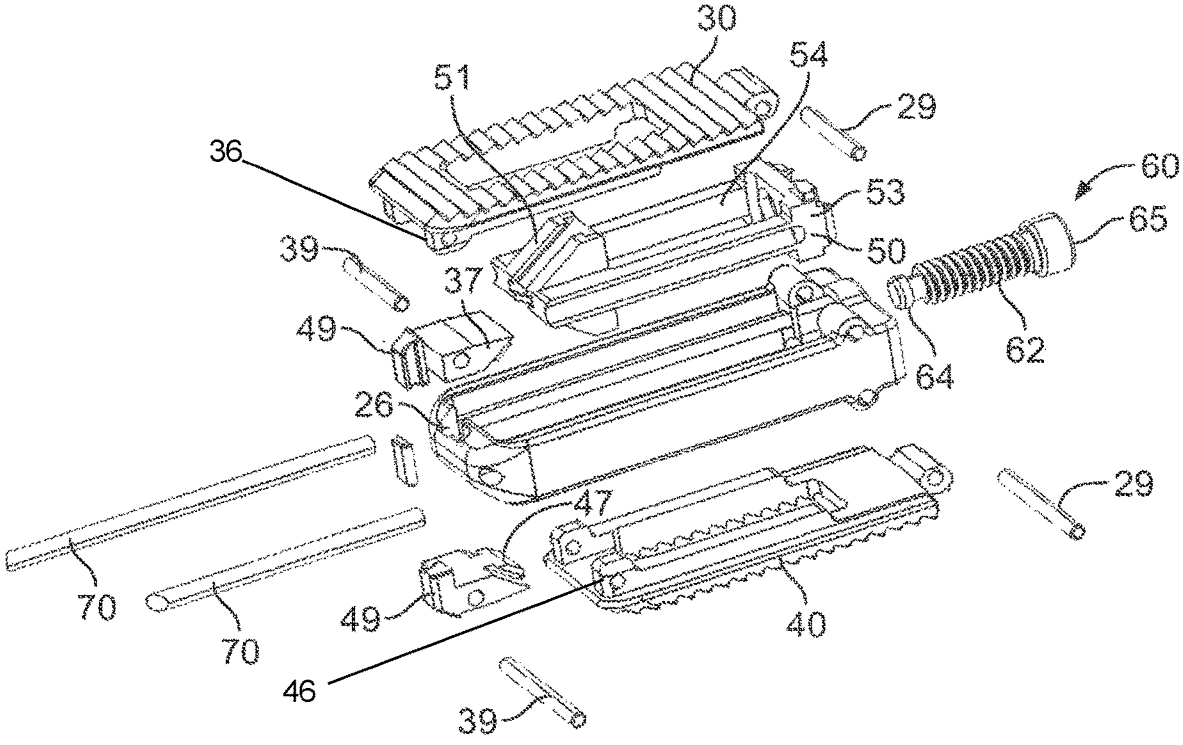
FIG. 11 is an exploded perspective view of the expandable spinal fusion implant of FIG. 1.

FIGS. 1-15 illustrate an exemplary embodiment of the expandable spinal fusion implant 10. The implant 10 includes a housing 20. The housing 20 is comprised of first and second lateral walls 22, 23, a distal or leading end wall 24 and a proximal or trailing end wall 25. The lateral walls 22, 23 and distal 24 and proximal 25 walls define a hollow interior of housing 20. According to this embodiment, the first and second lateral walls 22, 23 are of equal length and the length of the lateral walls 22, 23 spans the length of the implant 10. The distal wall 24 is tapered, increasing in height from the distal most point to the point where it meets the lateral walls 22, 23 to aid in insertion of the implant 10 into the disc space. As illustrated in the exemplary embodiment, the distal wall 24 may also include a slots 26 dimensioned to receive complementary projections 49 extending from the upper and lower endplates 30, 40. The slots comprise a first slot in the upper surface of the distal end 24 of the housing 20 for receiving a projection from the upper endplate 30 and a second slot in the lower surface of the distal end 24 of the housing 20 for receiving a projection 49 from the lower endplate 40. The proximal wall 25 of the housing is best illustrated in FIGS. 5 and 6. The proximal wall 25 includes two apertures. The first is a graft delivery port 27 and the second is a drive screw aperture 28. The drive screw aperture 28 is offset from the mid longitudinal axis of the implant 10 to facilitate packing of graft into the hollow interior of the housing 10 through the graft delivery port 27 upon implantation of the implant 10 into the disc space. The housing 20 has a static height that remains unchanged when the implant 10 is in its collapsed configuration and in its expanded configuration. The maximum height of the housing 20 is less than the maximum height of the overall implant 10.

According to the embodiment of FIGS. 1-15, the housing 20 is coupled to the upper and lower endplates 30, 40 via pins 29 adjacent the proximal end 15 of the implant 10. The upper and lower endplates 30, 40 have identical features as described below. Each endplate 30, 40 has a bone contacting surface 32, 42 and an interior surface 34, 44. The endplates 30, 40 have a width that is equal to the width of the overall implant and equal to the width of the housing 20. The perimeter of the interior surfaces 34, 44 of the endplates 30, 40 rests adjacent the lateral walls 22, 23 of the housing 20 when the implant 10 is in its collapsed configuration. The upper and lower endplates 30, 40 according to this embodiment are generally rectangular and include a central fusion aperture 35, 45. The central fusion apertures 35, 45 are in communication with the hollow interior of the housing 20 and the central fusion aperture 55 of the wedge 50 to allow for bone growth through the implant 10 after the implant 10 has been place within the disc space of a patient. The endplates further include anti-migration features 31, 41 on their respective bone contacting surfaces 32, 42. The interior surface 34, 44 of each endplate 30, 40 includes an extension 36, 46 coupled to the endplate 30, 40 via a pin 39. The extensions 36, 46 include a projection 39 at the distal end and a ramp 37, 47 at the proximal end. The ramps 37, 47 engage the superior and inferior angled surfaces 51, 52 on the wedge 50 to allow for expansion of the height of the implant 10 as the wedge 50 is driven distally within the implant 10. As illustrated in the exemplary embodiment of FIGS. 1-15, the ramps 37, 47 and angled surfaces 51, 52 of the wedge may include mating features to couple the wedge 50 to the endplates 30, 40. In the exemplary embodiment, this mating feature is a dovetail connection, though other mating features may be employed in the alternative.

As illustrated by the exemplary embodiment of FIGS. 1-15, the implant 10 includes a wedge 50 housed between the upper and lower endplates 30, 40 and within the hollow interior of the housing 20. The wedge 50 includes first and second opposing angled surfaces 51, 52 at its distal end and a drive block 53 at its proximal end. The opposing angled surfaces 51, 52 and drive block 53 are connected via a pair of lateral arms 54 extending therebetween. The opposing angled surfaces 51, 52, lateral arms 54 and drive block 53 reside inside the hollow interior of the housing 20 and define a central aperture 55 that is in communication with the central apertures 35, 45 of the upper and lower endplates 30, 40. Optionally, the lateral arms 54 of the wedge 50 may engage rails 70 that rest in between a recess in the exterior surface of the lateral arms 54 and the interior surface of the lateral walls 22, 23 of the housing 20. The drive block 53 includes a graft aperture 57 extending through its thickness. The graft aperture 57 of the drive block 53 is in communication with the graft delivery port 27 in the proximal wall 25 of the housing 20 to allow graft material to be pass through the housing 20 and wedge 50 into the interior of the implant 10. The drive block 53 also includes a receptacle 56 dimensioned to house the distal end 64 of the drive mechanism 60.

According to the exemplary embodiment of FIGS. 1-15, the drive mechanism 60 is a screw. The drive screw 60 has a proximal end 64 and a distal end 65 and a threaded shaft 62 extending between the proximal end 64 and the distal end 65. The proximal end 64 includes a mating feature 63 for engaging a driving tool (not shown). The distal end 65 is configured to complement the shape of the receptacle 56 of the drive block 53. The threaded shaft of 62 of the drive screw is configured to be received in a complementary threaded drive screw aperture 28 in the housing 20, such that as the drive screw 60 is rotated, it translates distally through the drive screw aperture 28 and consequently pushes the wedge 50 distally. When the wedge 50 is urged distally, the opposing angled surfaces 51, 52 engage the ramps 37, 47 on the endplates 30, 40 thereby increasing the distance between the distal ends of the endplates 30, 40 and increasing the distal height of the implant 10.

Figure 12:
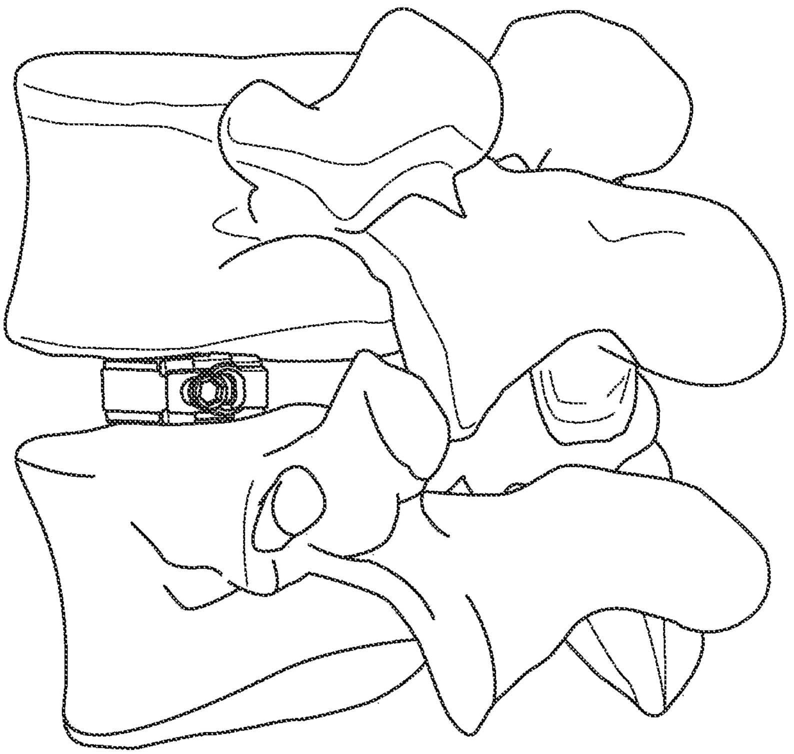
FIG. 12 is a perspective view of the expandable spinal fusion implant of FIG. 1 implanted into the intervertebral space of a spine.
Figure 13:
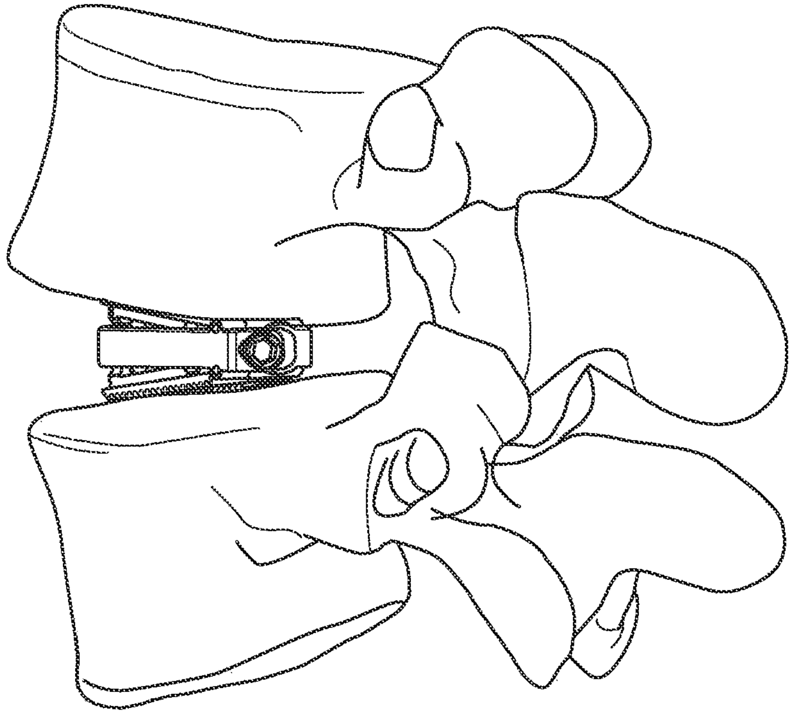
FIG. 13 is a perspective view of the expandable spinal fusion implant of FIG. 12 in its expanded configuration.
Figure 14:
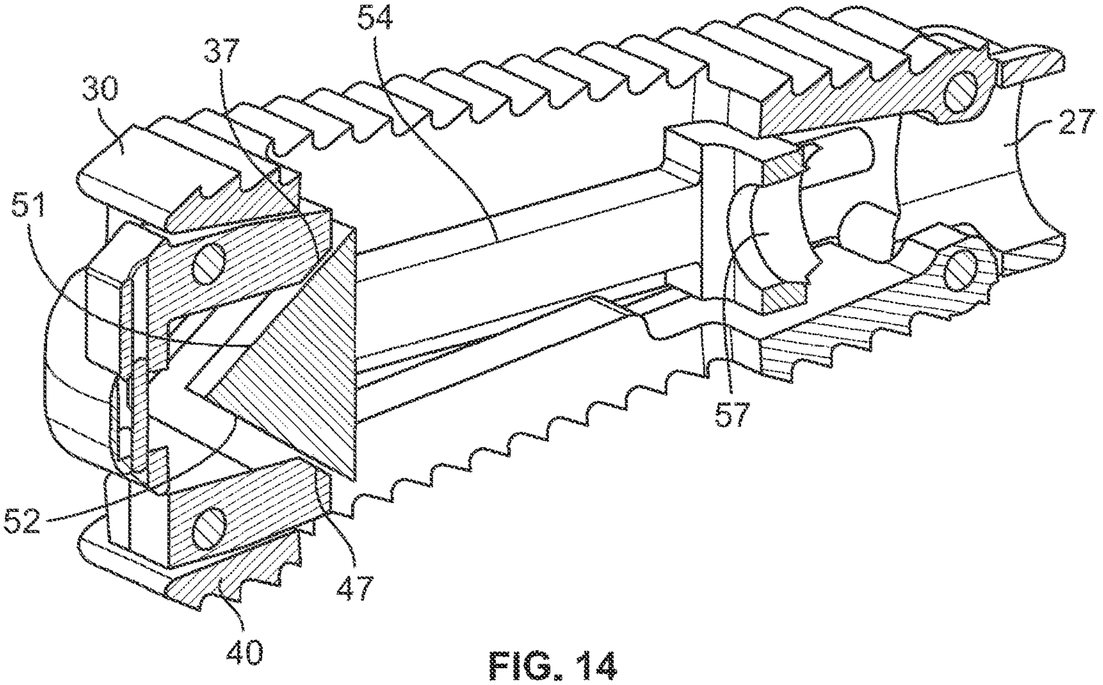
FIG. 14 is a perspective cross-sectional view of the expandable spinal fusion implant of FIG. 2.
Figure 15:
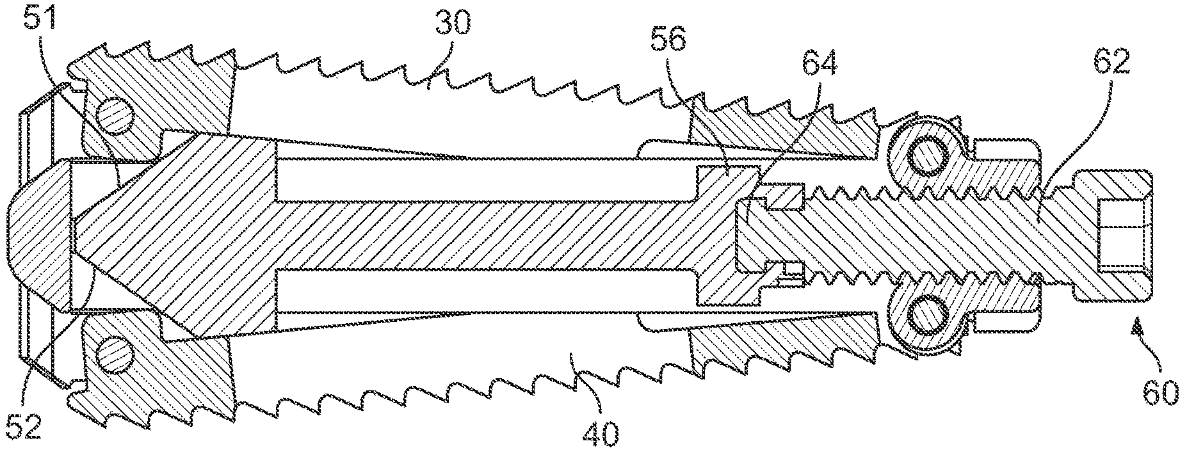
FIG. 15 is a side cross-sectional view of the expandable spinal fusion implant of FIG. 2.
Figure 16:
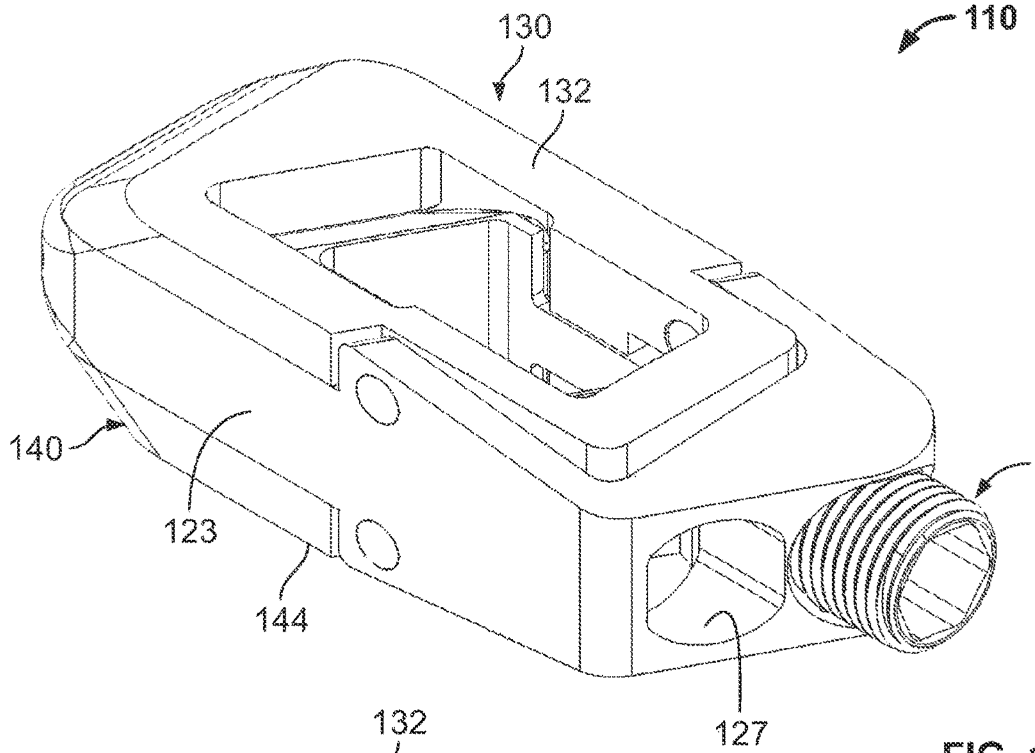
FIG. 16 is a perspective view of an expandable spinal fusion implant in a collapsed position according to an alternative embodiment.
Figure 17:
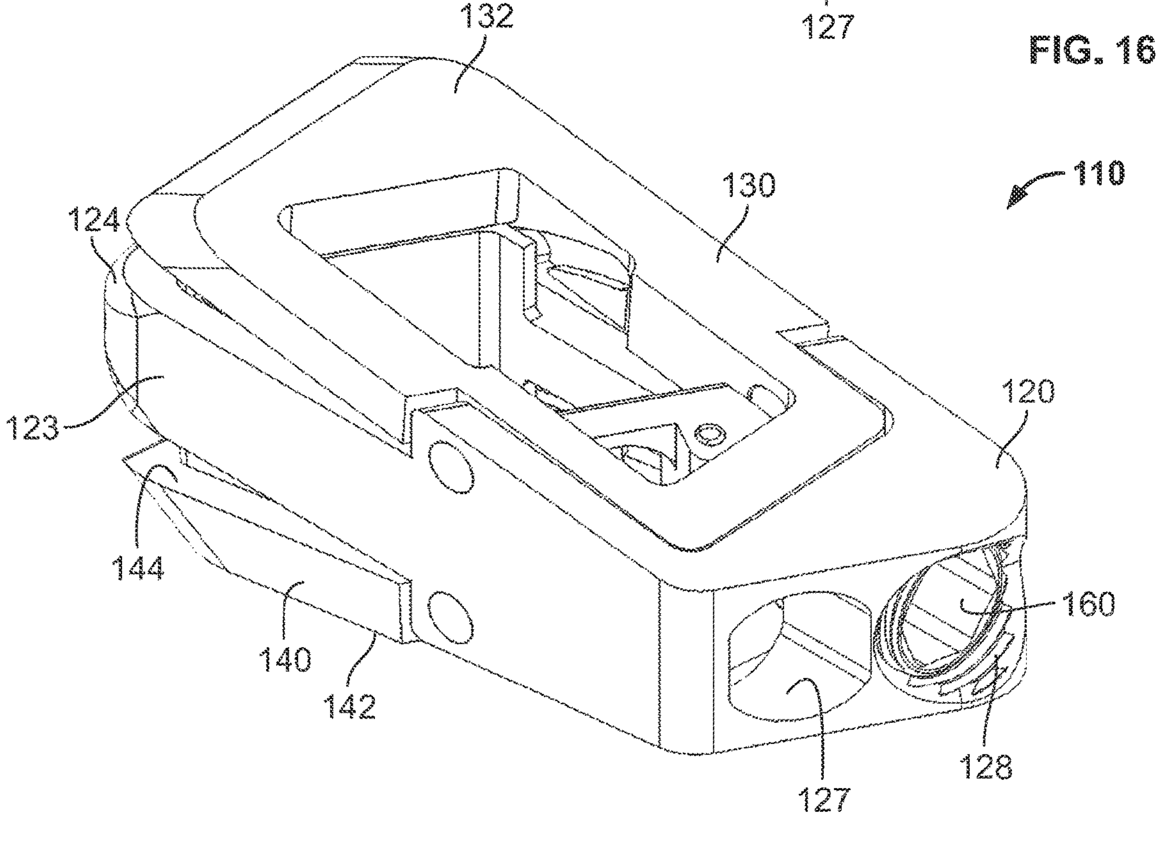
FIG. 17 is a perspective view of an expandable spinal fusion implant in an expanded configuration according to the alternative embodiment of FIG. 16.
Figure 18:
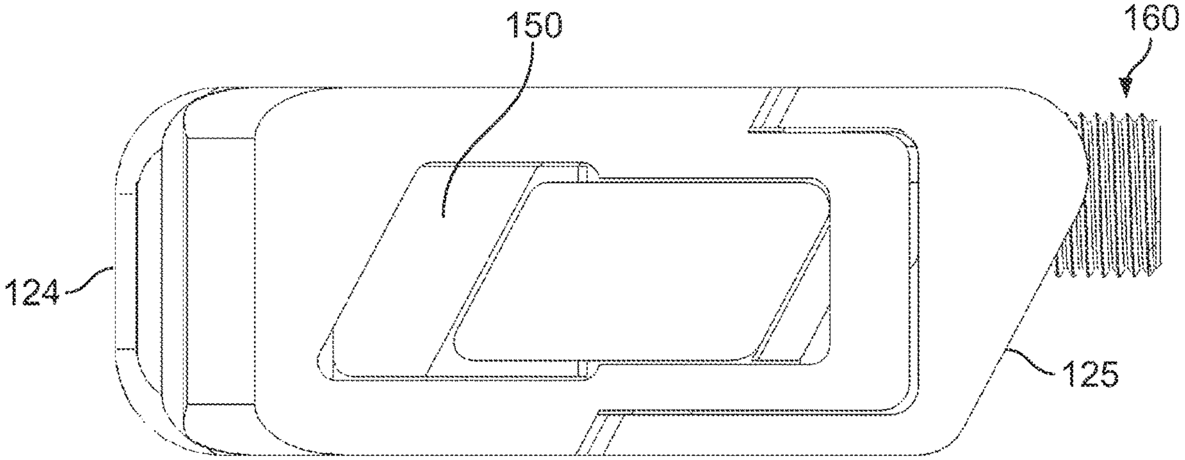
FIG. 18 is a top view of the expandable spinal fusion implant of FIG. 16.
Figure 19:
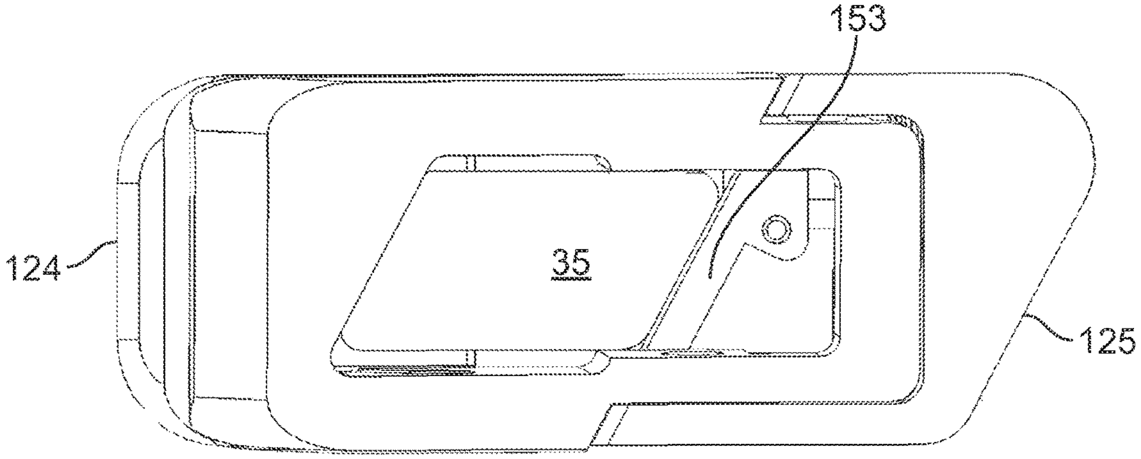
FIG. 19 is a top view of the expandable spinal fusion implant of FIG. 17.
Figure 20:
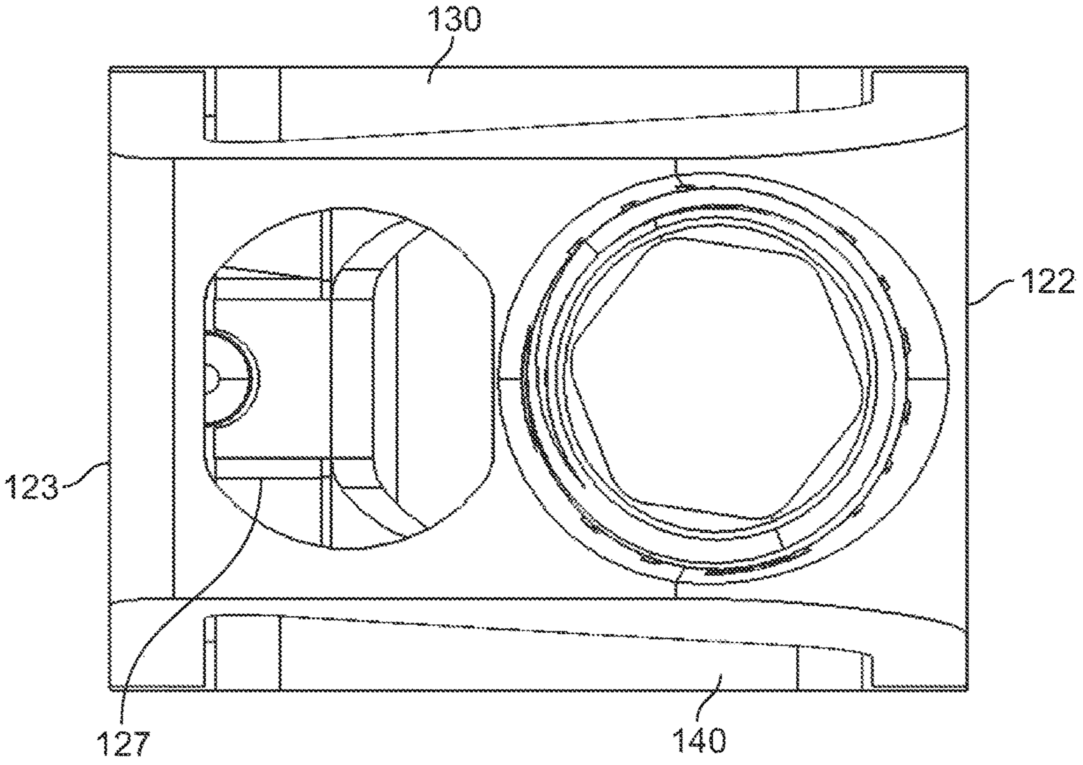
FIG. 20 is a back view of the expandable spinal fusion implant of FIG. 16.
Figure 21:
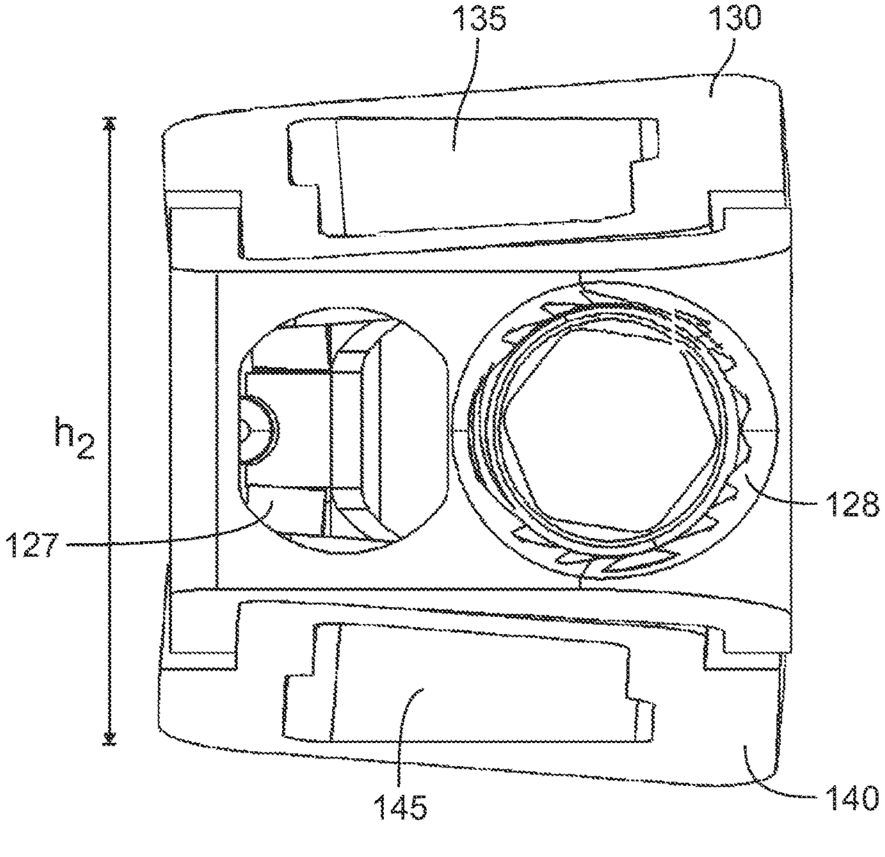
FIG. 21 is a back view of the expandable spinal fusion implant of FIG. 17.
Figure 22:
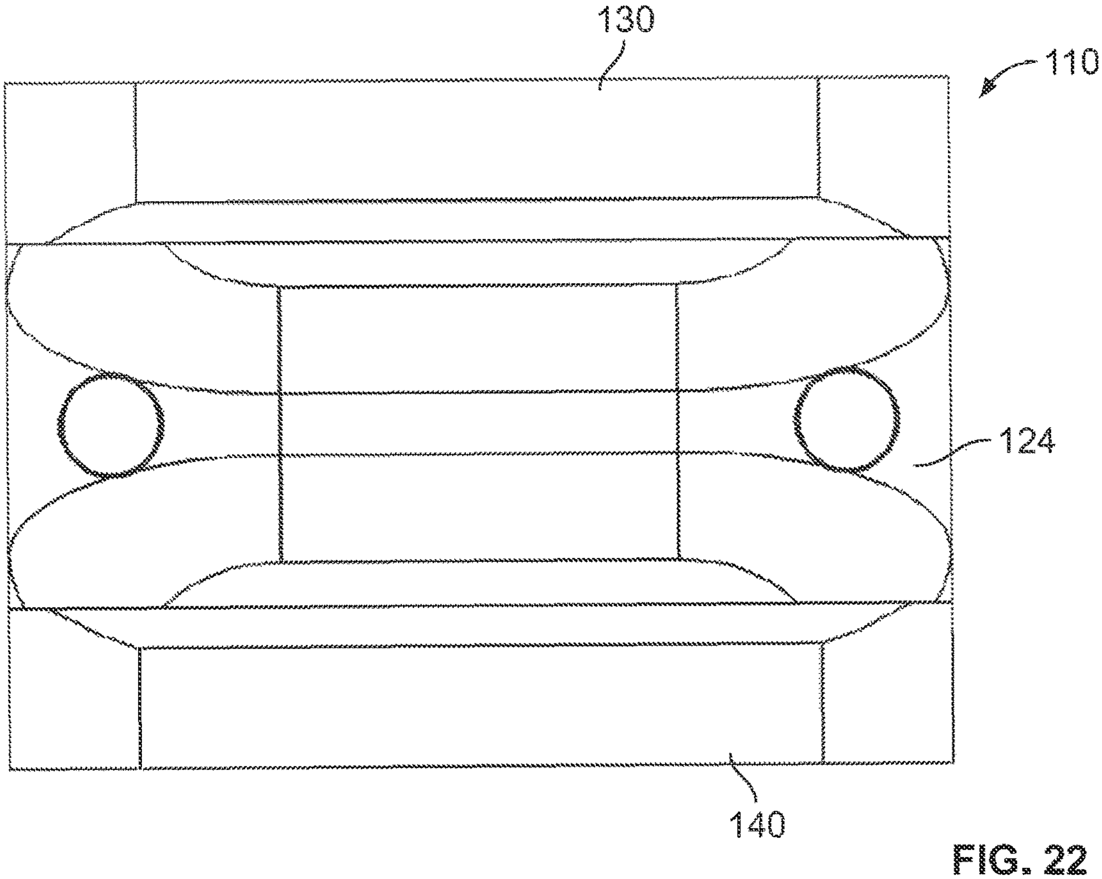
FIG. 22 is a front view of the expandable spinal fusion implant of FIG. 16.

In use according to this exemplary embodiment, the implant 10 implant is inserted into the disc space between adjacent vertebral bodies in its collapsed position as illustrated in FIG. 12. The collapsed configuration of the implant is illustrated in FIGS. 1, 3, 5, 7 and 9. Once the implant 10 has been placed in the desired position within the disc space, the drive screw 60 is engaged with a driving tool and rotated to advance the drive screw 60 distally within the implant, thereby advancing the wedge 50 distally and causing the upper and lower endplates 30, 40 to separate at the distal end 14 of the implant 10. When the drive screw has been fully advanced, the implant 10 is in its fully expanded configuration as illustrated in FIG. 13. Upon desired expansion of the implant, graft material is inserted into the interior of the implant through the graft delivery port 27 and graft aperture 57 of the wedge in the proximal end of the implant.

FIGS. 16-27 illustrate an alternative embodiment of the expandable spinal fusion implant 110. The implant 110 according to this alternative embodiment has many of the same features as described for the implant 10 in FIGS. 1-15 which are not necessarily repeated in detail here. The implant 110 according to the alternative embodiment shown in FIGS. 16-27 is an oblique implant, meaning it is dimensioned to be inserted into the disc space at an angle that is oblique to the midline of the disc space. For example, this implant insertion trajectory is common in a transforaminal lumbar interbody fusion (TLIF) surgical procedure. The implant 110 according to the alternative embodiment is similar in structure to the one described in FIGS. 1-15 in that it includes a housing 120, upper and lower endplates 130, 140, a wedge 150 and a drive mechanism 160 which are described in further detail below.

According to the embodiment of FIGS. 16-27, the implant 110 has a housing 120. The housing has the same structure as previously described, including a distal wall 124, a proximal wall 125 and first and second lateral walls 122, 123 extending between the distal and proximal walls 124, 125. The four walls define a hollow interior of the housing 120. However, the housing 120 according to the alternative embodiment is different in that the first lateral wall 122, the anterolateral wall when the implant 120 is positioned in the disc space, is greater in length than the second lateral wall 123 (the posterolateral wall). The distal wall 124 is tapered to aid in insertion of the implant 110 into the disc space. The proximal wall 125 includes a threaded drive screw aperture 127 and a graft delivery port 128. The drive screw aperture 127 is offset from the midline of the implant 110 and configured to receive the drive mechanism 160 therethrough. The height of the housing 120 is static, remaining unchanged when the implant 110 is in its collapsed configuration and its expanded configuration. The maximum height of the housing 120 is less than the maximum height of the overall implant 110.

Figure 23:
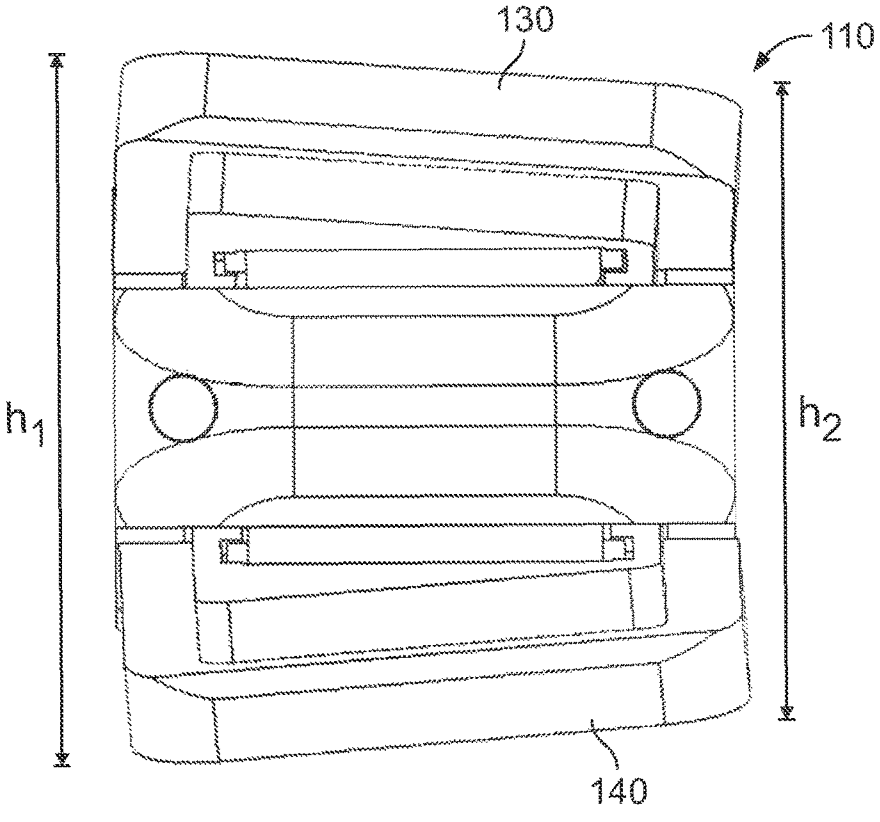
FIG. 23 is a front view of the expandable spinal fusion implant of FIG. 17.
Figure 24:
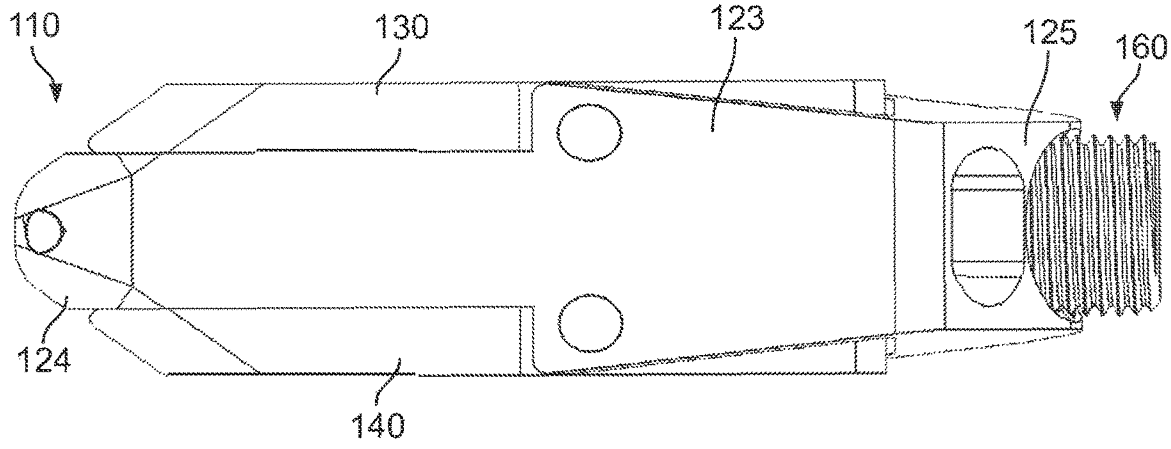
FIG. 24 is a first side view of the expandable spinal fusion implant of FIG. 16.
Figure 25:
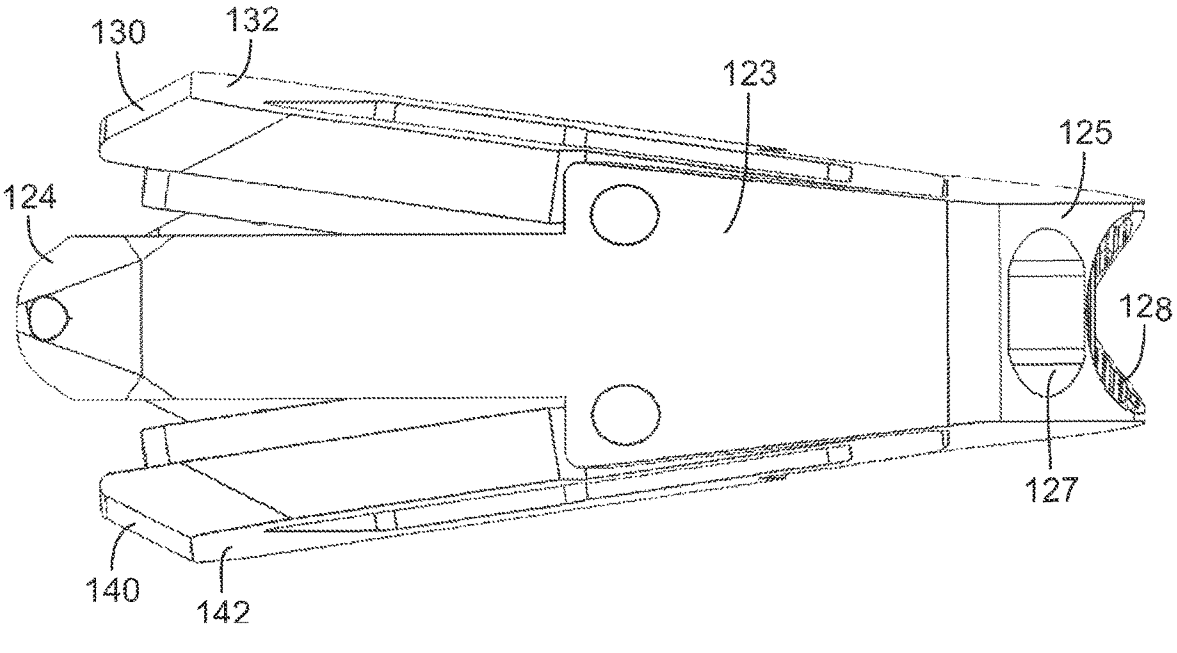
FIG. 25 is a first side view of the expandable spinal fusion implant of FIG. 17.
Figure 26:
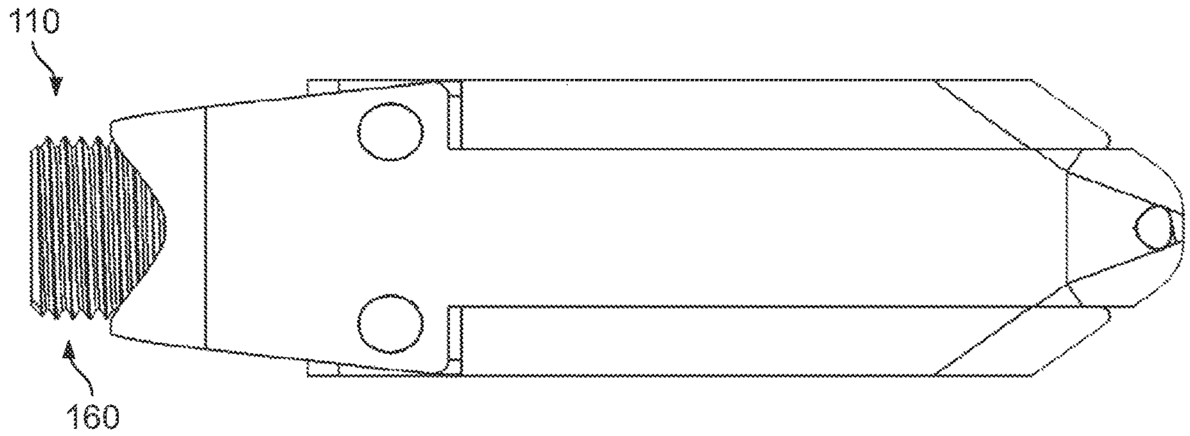
FIG. 26 is a second side view of the expandable spinal fusion implant of FIG. 16.
Figure 27:
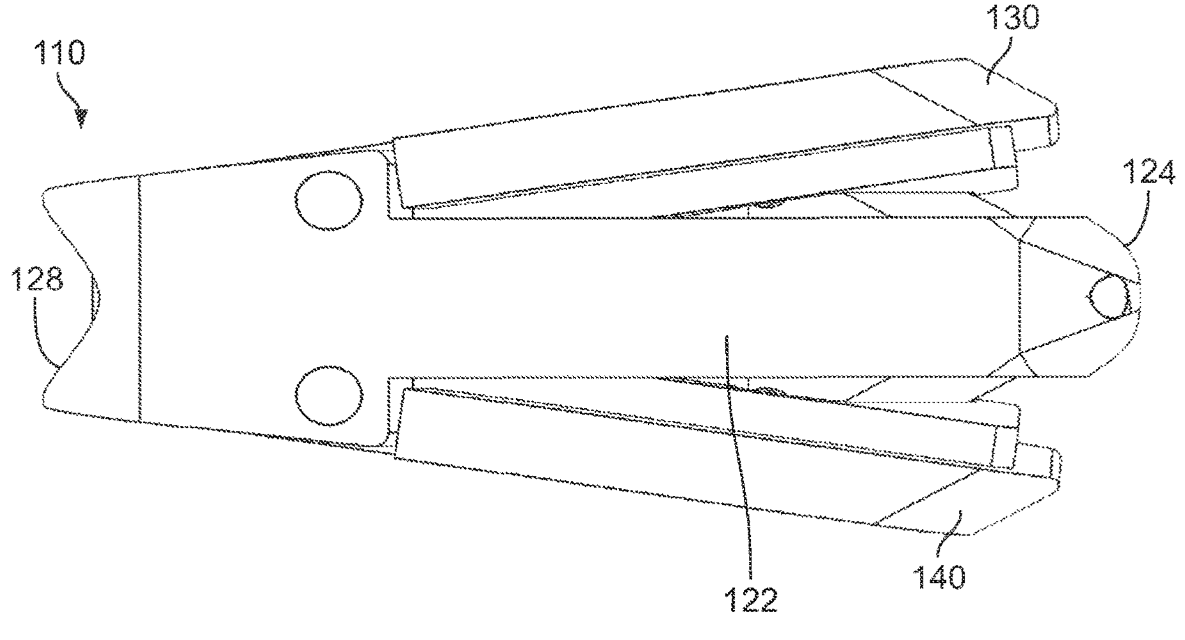
FIG. 27 is a second side view of the expandable spinal fusion implant of FIG. 17.
Figure 28:
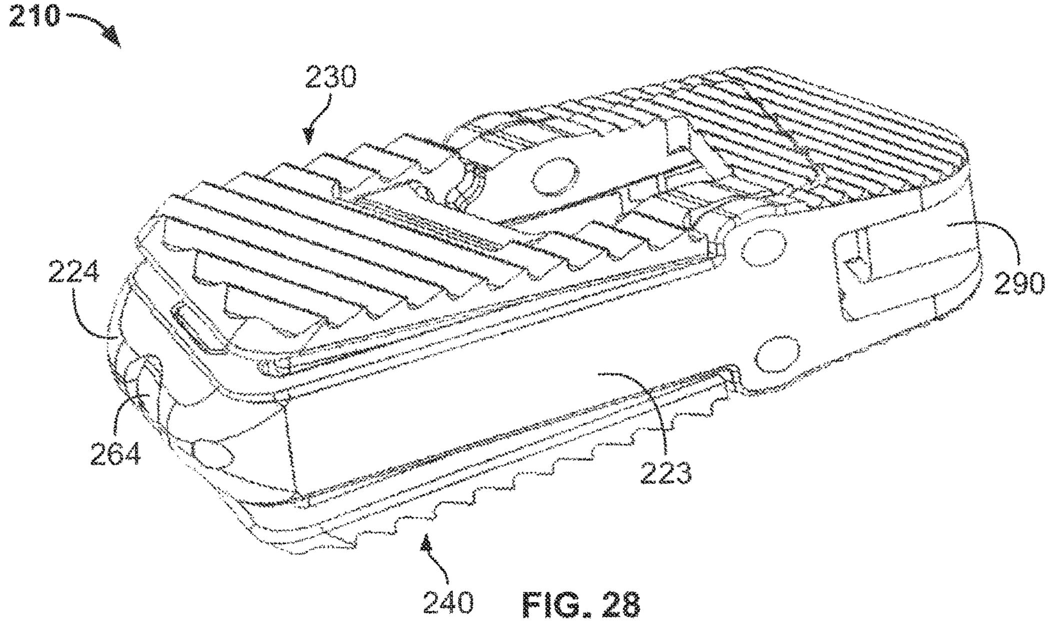
FIG. 28 is a perspective view of an expandable spinal fusion implant according to another alternative embodiment.
Figure 29:
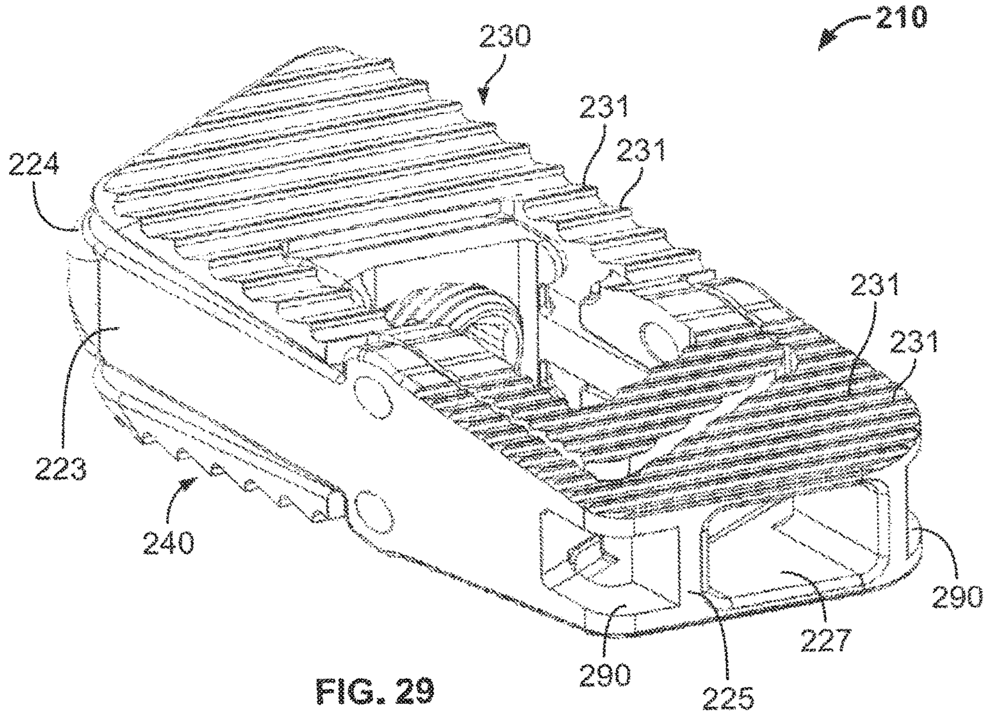
FIG. 29 is a rear perspective view of the expandable spinal fusion implant of FIG. 28.
Figure 30:
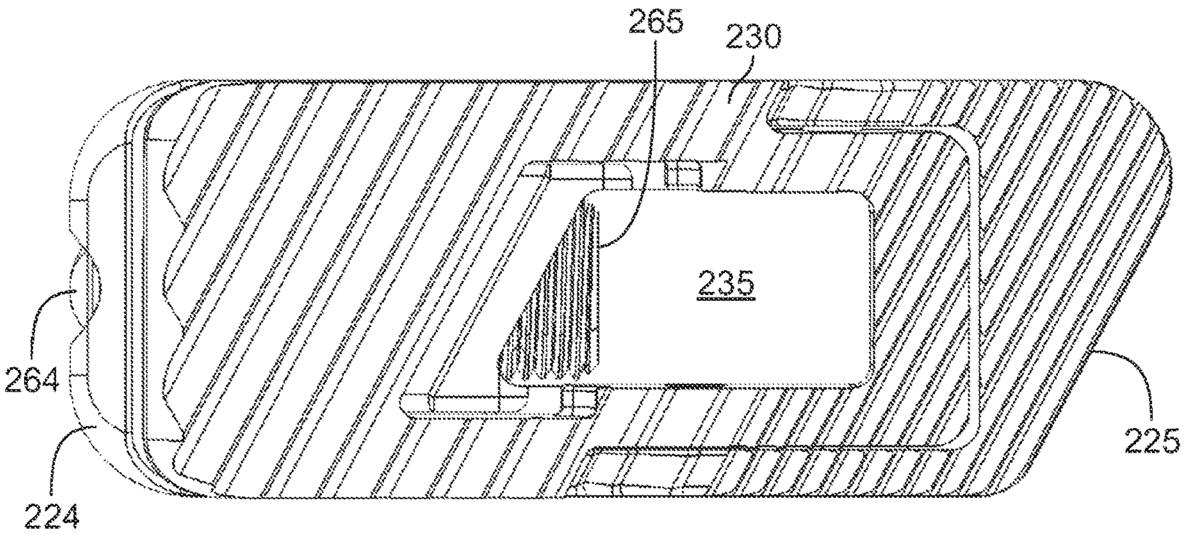
FIG. 30 is a top view of the expandable spinal fusion implant of FIG. 28.
Figure 31:
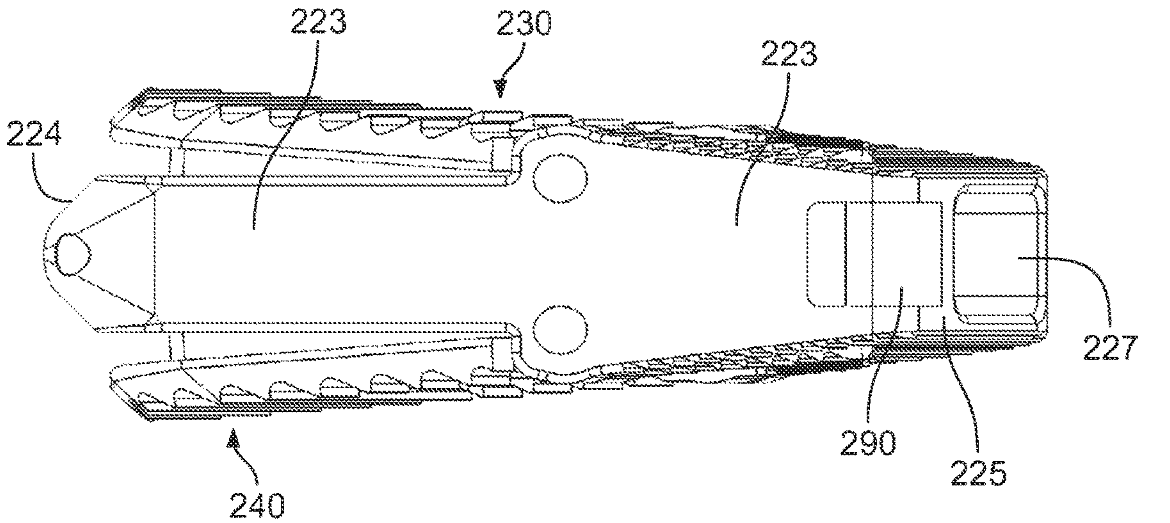
FIG. 31 is a first side view of the expandable spinal fusion implant of FIG. 28.
Figure 32:
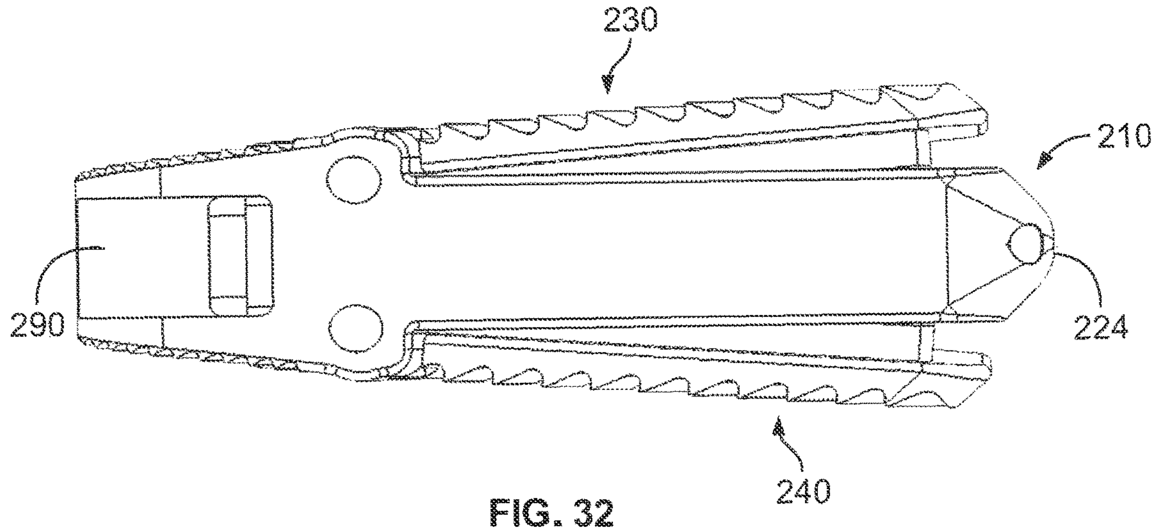
FIG. 32 is a second side view of the expandable spinal fusion implant of FIG. 28.

The upper and lower endplates 130, 140 according to this alternative embodiment are identical, mirror images of each other. The endplates 130, 140 of the alternative embodiment differ from the endplates 30, 40 of the previously described embodiment in that they increase in height across the endplate 130, 140 from the proximal end 133, 143 to the distal end 131, 141 of the endplate 130, 140 and from the posterolateral side 136, 146 to the anterolateral side 138, 148 of the endplate 130, 140. As a result, when the implant 120 is in its fully expanded configuration, the anterolateral height $h_1$ of the implant 110 is greater than the posterolateral height $h_2$ of the implant, as best shown in FIGS. 23 and 25. Each endplate 130, 140 further comprises a bone contacting surface 132, 142 and an interior surface 134, 144. Although not illustrated in FIGS. 16-27, it is contemplated that the bone contacting surfaces 132, 142 could include antimigration features. The interior surfaces 134, 144 of the endplates 130, 140 include a ramped surface 137, 147 at the distal end of the endplate 131, 141 that engage opposing angled surfaces 151, 152 on the wedge 150. According to the embodiment shown in FIGS. 16-27, the interior side surfaces of the endplates include slots 139, 149 for receiving projections 126 on the sides of the wedge 150.

According to the alternative embodiment, the wedge 150 is similar in structure to the wedge 50 as previously described. The wedge 150 has opposing angled surfaces 151, 152 at its distal end and a drive block 153 at its proximal end. The opposing angled surfaces 151, 152 and drive block 153 are coupled via a pair of lateral arms 154 defining a central aperture 155 therebetween. The drive block 153 similarly includes a graft aperture 157 through its thickness and a drive screw receptacle 158 dimensioned to house the distal end 164 of the drive screw 160.

The drive mechanism 160 of this alternative embodiment is similar in form and in function to the drive screw mechanism 60 described for the previous embodiment. The drive mechanism 160 is a drive screw. The drive screw 160 has a distal end 164 dimensioned to be received within the receptacle 158 of the drive block 153 and a proximal end 165 equipped with a mating feature for engaging a drive tool (not shown) and a threaded shaft 162 extending between the proximal end and distal end. As the drive screw 162 is rotated, the threads on the shaft 162 engage the complementary threads on the drive screw aperture 128 of the housing 120 allowing the drive screw to translate distally into the implant 110 thereby urging the wedge 150 distally within the implant and causing the endplates 130, 140 to separate.

FIGS. 28-36 illustrate yet another alternative embodiment of an expandable spinal fusion implant 210 in a partially expanded state. As with the embodiment illustrated in FIGS. 16-27, the current embodiment is designed to be an oblique implant for use in a TLIF procedure. The embodiment illustrated in FIGS. 28-36 includes the same basic structures as the two previous embodiments, including a housing 220, upper and lower endplates 230, 240, a wedge 250 and a drive mechanism 260. These structures are described in further detail in the following paragraphs.

According to the third embodiment of FIGS. 28-36, the implant 210 includes a housing 220. The housing 220 has a distal wall 224, a proximal wall 225 and first and second lateral walls 222, 223 defining a hollow interior. The distal wall 224 of the housing 220 is tapered from where it meets the lateral walls 222, 223 to the distal most point of the distal wall to aid in insertion of the implant 210 into the disc space. The distal wall 224 includes a drive mechanism aperture 228 configured to receive the distal end of the drive mechanism 260. The proximal wall 225 has first and second bone contacting surfaces 229 and a graft delivery port 227 extending through its thickness. The proximal wall 225 may also include channels 290 for receiving arms of an insertion tool (not shown) As illustrated in FIGS. 28-36, it is contemplated that the bone contacting surfaces 229 of the proximal wall 225 include anti-migration features 231, 241. The height of the housing 220 is static, remaining unchanged when the implant 210 is in its collapsed configuration and in its expanded configuration. The first lateral wall 222, the anterolateral wall of the implant when the implant is positioned within the disc space, has a length that is greater than the length of the second lateral wall 223 (the posterolateral wall). It is contemplated that the housing 220 can be manufactured of metal or PEEK.

Figure 33:
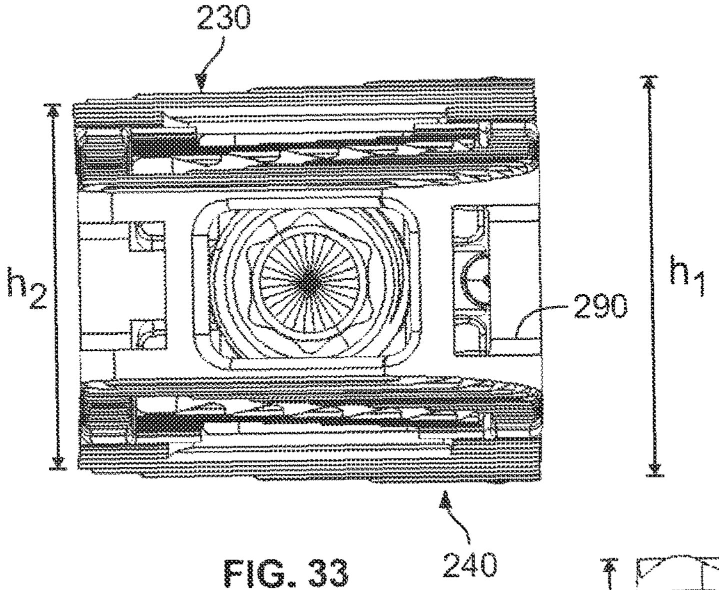
FIG. 33 is a back view of the expandable spinal fusion implant of FIG. 28.
Figure 34:
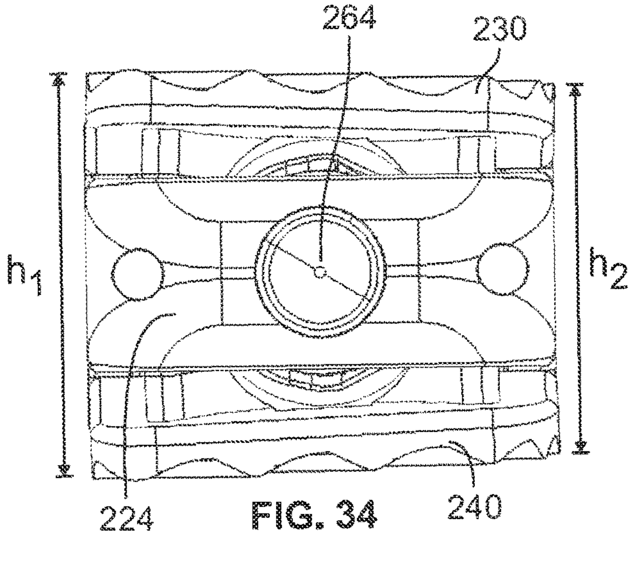
FIG. 34 is a front view of the expandable spinal fusion implant of FIG. 28.
Figure 35:
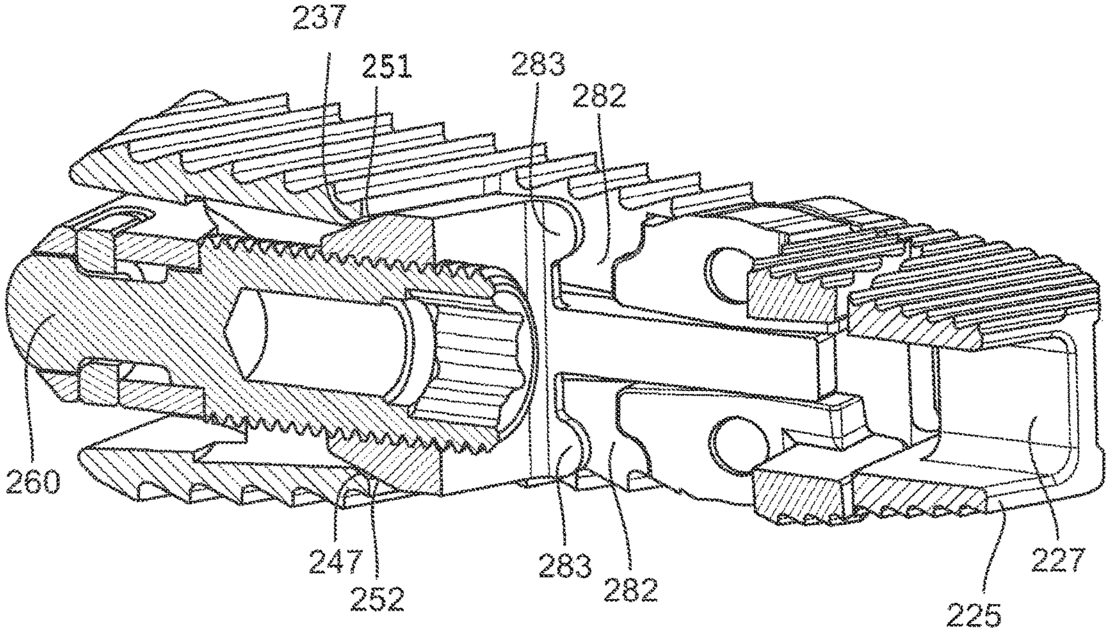
FIG. 35 is a perspective cross-sectional view of the expandable spinal fusion implant of FIG. 28.
Figure 36:
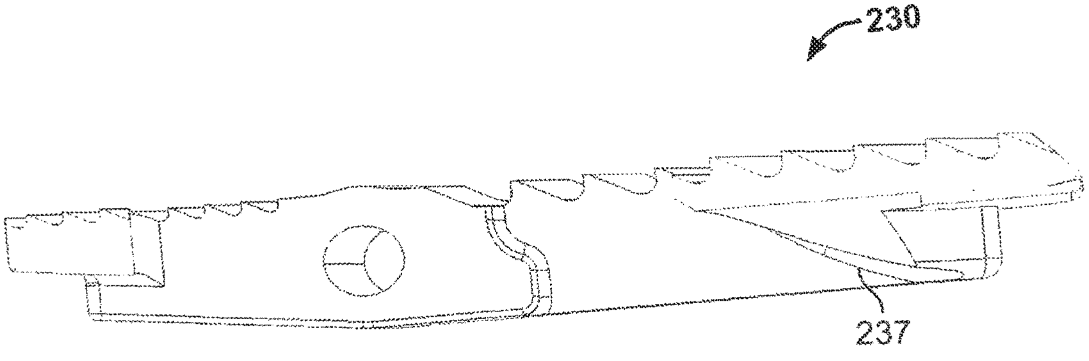
FIG. 36 is a side cross-sectional view of the upper endplate of the expandable spinal fusion implant of FIG. 28.

According to the embodiment shown in FIGS. 28-36, the housing is coupled to the upper and lower endplates 230, 240 via pins 239. The upper and lower endplates 230, 240 are identical, mirror images of each other. Each endplate 230, 240 has a bone contacting surface 232, 242 and an interior surface 234, 244. The bone contacting surfaces 232, 242 may include anti-migration features 239. The endplates 230, 240 include a central fusion aperture 235, 245 in communication with the hollow interior of the housing 220 to allow bone growth through the implant 210 after the implant has been placed within the disc space of patient. Each endplate 230, 240 further includes an interior side walls 272, 273 having a recess 282 and a projection 283 for engaging proximal projections 259 on the wedge 260. When the projections 283 on the interior side walls 272, 273 of the endplates are engaged with the proximal projections 259 on the wedge 250, the upper and lower endplates 230, 240 are locked in the collapsed configuration until such time as the wedge 260 is translated distally and the projections 283, 259 are disengaged. The interior surfaces 234, 244 of the endplates 230, 240 include a ramp 237, 247 adjacent the distal end of the endplates 230,240 that engage the opposing angled surfaces 251,252 on the wedge 250 to facilitate the expansion of the distal end 214 of the implant 210. As best illustrated in FIG. 36, the ramp 237, 247 is slightly radiused. While illustrated here as having a radiused ramp 237 and a generally planar angled surface 251, 252 on the wedge, it is contemplated that the ramp 237, 247 could be planar and the opposing angled surfaces 251, 252 on the wedge could be radiused. Alternatively, it is contemplated that both the ramp 237, 247 and the opposing angled surfaces 251, 252 could be planar or both could be radiused. As best seen in FIGS. 33 and 34, the endplates 230, 240 have a greater height on the anterolateral sides 232, 242 of the distal ends 234, 244 of the end plates such that when the implant is in its fully expanded state, the overall height of the implant is both greater at the distal end of the implant than at the proximal end of the implant but also the height $h_1$ on the anterolateral side of the implant is greater than the height $h_2$ on the posterolateral side of the implant.

The wedge 250 according to the third embodiment is housed in the hollow interior of the housing 220 and between the interior surfaces 234, 244 of the upper and lower endplates 230, 240. The wedge 250 has a distal face defined by opposing angled surfaces 251, 252 and a proximal face 293. The wedge has a threaded drive mechanism aperture 258 extending throughout the wedge from the proximal face 243 through the distal face dimensioned to receive a threaded shaft 262 of the drive mechanism 260. As previously mentioned, the wedge has projections 259 extending from the proximal face 293 for engaging projections 283 on the interior side walls 272, 273 of the endplates 230, 240. The wedge 250 is positioned in the interior of the implant 210 such that when the implant 210 is in its collapsed configuration the wedge 250 is sitting in the hollow interior and blocking the distal portion of the central fusion apertures 235, 245 of the endplates 230, 240. When the implant 210 is in its fully expanded configuration, the wedge has been urged distally and thus is blocking less of the central fusion apertures 235, 245 effectively increasing the size of the aperture extending through the implant 210.

According to the embodiment shown in FIGS. 28-36, the drive mechanism 260 includes a threaded shaft 262 having a proximal end 265 including an engagement feature 267 for mating with a drive tool (not shown). The distal portion 264 of the drive mechanism 260 extends distally from the threaded shaft 262 and is configured to be anchored in the distal wall 224 of the housing 220. The distal portion of the drive mechanism 260 is non-threaded, and is allowed to rotate within the drive mechanism aperture 227 in the distal wall 224 of the housing without translating. As the drive mechanism 260 is rotated by a drive tool, the threaded shaft engages complementary threads inside the threaded aperture 258 extending through the wedge 250 and causes the wedge 250 to translate distally until the implant 210 is fully expanded.

In use, the expandable spinal fusion implant 210 is inserted into a disc space between adjacent vertebral bodies in its collapsed configuration. Although not shown, it is contemplated that an insertion tool having two arms extending from the distal end will engage the insertion tool channels 290 on the proximal wall 225 of the housing 220. The insertion tool has a hollow shaft to allow the drive mechanism driver to be inserted therethrough. The distal end of the drive mechanism driver is inserted through the graft delivery port 227 in the housing 220 and engaged with the mating feature 267 of the drive mechanism 267. The drive mechanism driver is used to rotate the drive mechanism thereby causing the wedge 260 to translate distally between the upper and lower endplates 230, 240. Then the driver is disengaged from the drive mechanism and withdrawn from the hollow shaft of the insertion tool. Subsequently, graft material is inserted through the hollow shaft of the insertion tool, through the graft delivery port 227 in the proximal wall 224 of the housing 220 and into the hollow interior of the implant 210. In an exemplary embodiment, a sufficient amount of graft is inserted to fill the interior of the implant, through the central apertures 235, 245 in the endplates such that there is graft in compact contact with the endplates of each of the adjacent vertebral bodies.

A number of embodiments of the invention have been described. Nevertheless, it will be understood that various modifications may be made without departing from the spirit and scope of the invention. Accordingly, other embodiments are within the scope of the following claims.

The invention claimed is:

1. An expandable implant comprising:

a housing comprising a proximal wall and a distal wall comprising an upper slot and a lower slot;

an upper endplate moveably attached to the housing;

a lower endplate moveably coupled to the housing;

a wedge positioned at least partially within the housing, the wedge including a superior angled surface and an inferior angled surface;

an upper extension pivotably coupled to a distal end of the upper endplate and comprising a ramp at a proximal end configured to engage the superior angled surface of the wedge and a projection at a distal end configured to be received by the upper slot of the distal wall of the housing; and a lower extension pivotably coupled to a distal end of the lower endplate and comprising a ramp at a proximal end configured to engage the inferior angled surface of the wedge and a projection at a distal end configured to be received by the lower slot of the distal wall of the housing.

2. The expandable implant of claim 1, wherein the upper endplate comprises an interior surface comprising a ramp and the lower endplate comprises an interior surface comprising a ramp, and the wedge comprises a first surface configured to engage the ramp of the upper endplate and a second surface configured to engage the ramp of the lower endplate.

3. The expandable implant of claim 1, comprising a drive mechanism configured to engage the proximal wall of the housing and drive the wedge relative to the housing to move the expandable implant from a collapsed configuration to an expanded configuration.

4. The expandable implant of claim 3, wherein in the expanded configuration, a height between the upper endplate and the lower endplate increases along a direction from the proximal wall toward the distal wall of the housing, and wherein the distal wall of the housing is free of the drive mechanism.

5. The expandable implant of claim 3, wherein in the expanded configuration, a height between the upper endplate and the lower endplate increases along a direction from a posterolateral sidewall toward an anterolateral sidewall of the housing.

6. The expandable implant of claim 3, wherein the upper endplate and the lower endplate each comprise an interior side wall having a recess and a projection configured to engage the wedge and lock the upper endplate and the lower endplate in the collapsed configuration.

7. The expandable implant of claim 1, wherein the upper endplate includes a first opening and the lower endplate includes a second opening, wherein the first opening and second opening collectively form a fusion aperture extending through the housing between the upper endplate and the lower endplate.

8. The expandable implant of claim 7, wherein the wedge defines a wall of the fusion aperture such that a size of the fusion aperture increases as the implant is moved from the collapsed configuration to the expanded configuration.

9. The expandable implant of claim 3, wherein the drive mechanism includes a shaft with a first end rotatably coupled to the proximal wall of the housing and a second end threadedly coupled to the wedge.

10. The expandable implant of claim 9, wherein the wedge comprises an aperture extending from a proximal face to a distal face of the wedge and dimensioned to receive the second end of the shaft of the drive mechanism.

* * * * *